US012690898B2

(12) United States Patent
Srour et al.

(10) Patent No.: US 12,690,898 B2
(45) Date of Patent: Jul. 28, 2026

(54) IMPLANT DEVICE FOR A FACET JOINT AND METHOD FOR FUSING THE FACET JOINT

(71) Applicant: SC MEDICA, Strasbourg (FR)

(72) Inventors: Robin Srour, Strasbourg (FR); Camille Srour, Paris (FR)

(73) Assignee: SC MEDICA, Strasbourg (FR)

( * ) Notice: Subject to any disclaimer, the term of this patent is extended or adjusted under 35 U.S.C. 154(b) by 0 days.

(21) Appl. No.: 18/755,496

(22) Filed: Jun. 26, 2024

(65) Prior Publication Data

US 2024/0358415 A1      Oct. 31, 2024

Related U.S. Application Data

(63) Continuation-in-part of application No. 16/631,602, filed on Jan. 16, 2020, now abandoned.

(51) Int. Cl.
| | |
|---|---|
| *A61B 17/70* | (2006.01) |
| *A61F 2/30* | (2006.01) |
| *A61F 2/44* | (2006.01) |

(52) U.S. Cl.
CPC ........ *A61B 17/7064* (2013.01); *A61F 2/4405* (2013.01); *A61F 2/446* (2013.01); *A61F 2002/30841* (2013.01)

(58) Field of Classification Search
CPC ............. A61F 2/44–447; A61F 2/4405; A61B 17/7064
See application file for complete search history.

(56) References Cited

U.S. PATENT DOCUMENTS

| | | | | |
|---|---|---|---|---|
| 7,276,081 B1 * | 10/2007 | Coates | .................... | A61F 2/447 |
| | | | | 606/86 A |
| 2008/0161810 A1 * | 7/2008 | Melkent | ............. | A61B 17/1757 |
| | | | | 606/79 |
| 2013/0073046 A1 * | 3/2013 | Zaveloff | ................. | A61F 2/447 |
| | | | | 623/17.16 |
| 2020/0138589 A1 * | 5/2020 | Abbasi | .................... | A61F 2/447 |

* cited by examiner

*Primary Examiner* — Nicholas J Plionis
(74) *Attorney, Agent, or Firm* — Craft Chu PLLC; Andrew W. Chu

(57) ABSTRACT

An implant device for a facet joint includes a wedge portion and an anchor portion. The anchor portion is made integral with the wedge portion so as to form a central opening. The anchor portion includes a first face, a second face, and a lateral rim so as to form a rectangular prism portion. The first face is on a first longest and widest side of the rectangular prism portion. The second face is on a second longest and widest side of the rectangular prism portion. The method of fusing vertebrae with the implant device includes the step of forming a rectangular cavity between an upper vertebra and a lower vertebra. The rectangular cavity has a first longest and widest side on the upper vertebra and a second longest and widest side on the lower vertebra corresponding to the first face and the second face.

7 Claims, 3 Drawing Sheets

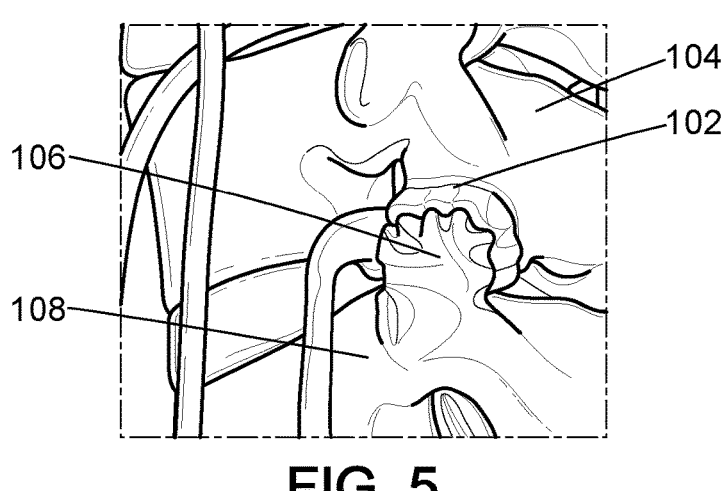
FIG. 5
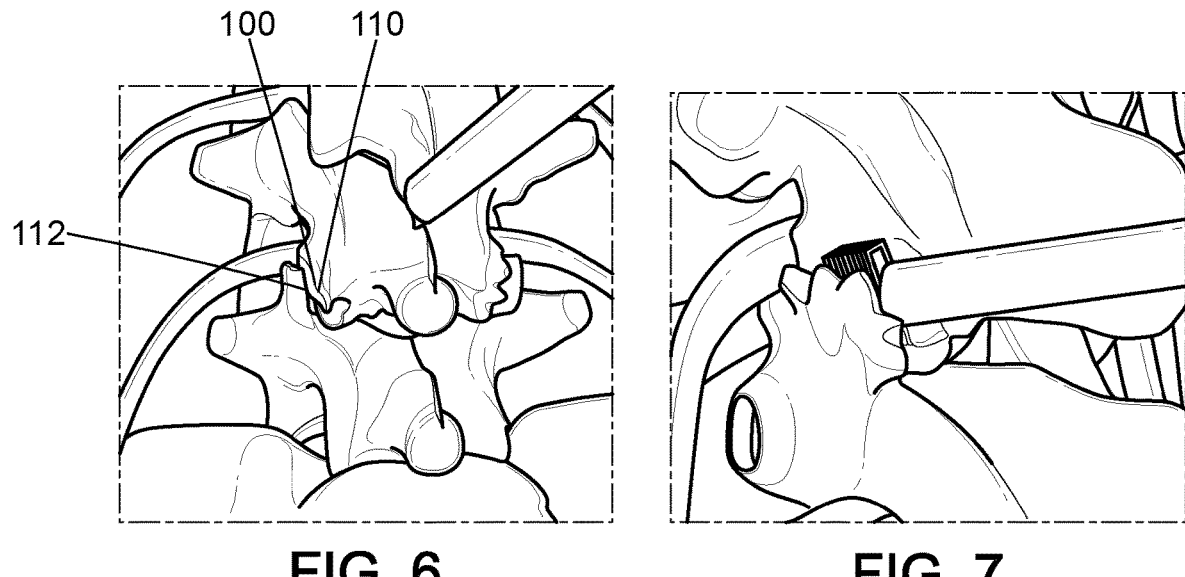
FIG. 6                    FIG. 7
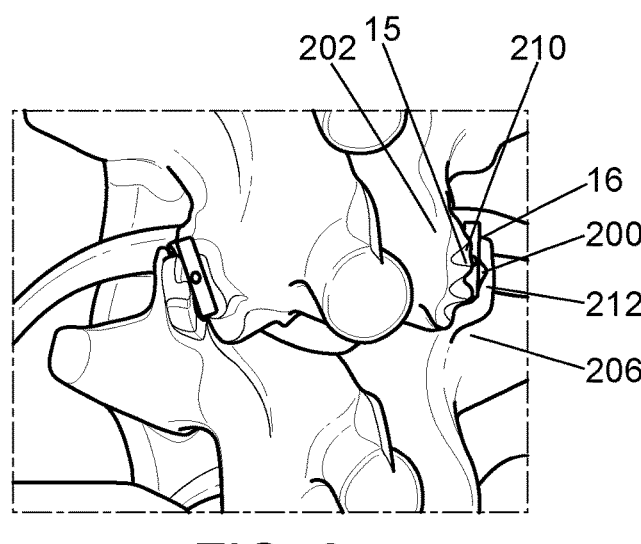
FIG. 8

IMPLANT DEVICE FOR A FACET JOINT AND METHOD FOR FUSING THE FACET JOINT

CROSS-REFERENCE TO RELATED APPLICATIONS

The present application claims priority under 35 U.S.C. Section 120 from U.S. patent application Ser. No. 16/631, 602, filed on 16 Jan. 2020, entitled "IMPLANT DEVICE FOR PERFORMING POSTERIOR SPINAL ARTHROD-ESIS AT A FACET JOINT".

STATEMENT REGARDING FEDERALLY SPONSORED RESEARCH OR DEVELOPMENT

Not applicable.
See also Application Data Sheet.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to an implant device for performing a posterior spinal arthrodesis at a facet joint. The present invention further relates to a method of fusing the facet joint with the implant device.

2. Description of Related Art Including Information Disclosed Under 37 CFR 1.97 and 37 CFR 1.98

Spinal arthrodesis or spinal fusion surgery connects at least two bones in the spine. The spinal fusion surgery of vertebrae has many variations with different effects on the body and facets of each vertebra. From the anterior, the disc between vertebrae can be removed so that the two vertebrae fuse together in the most conventional procedure. This anterior surgery is performed through the patient, so the risk to internal organs and peritoneum are heightened. Thus, other variations of the spinal fusion surgery change the orientation for better patient outcomes and recovery. From the posterior, a facet of a vertebra can be removed so that surgical tools can access the disc adjacent to the vertebra. The disc can be removed from the posterior, and the two vertebrae will fuse together. More or less of the facet joint can be removed. It may be too unstable to remove the entire facet joint or more than one side of facet joints on a vertebra. The prior art, including USPub20200138589, USPub20110230965, USPub20080288076, FR2946245 and WO 02/03895, disclose implant devices, such as interver-tebral cages and osteosynthesis bars/plates, suitable for being placed in the intervertebral space between the bodies of adjacent vertebrae, after removal of the disc. In combi-nation with pedicle screws or bone screws through facets, the prior art fuses two vertebrae with bone growth through the bodies of the vertebrae and the implant device. The facets of an upper vertebra are anchored to the facets of a lower vertebra, such as each lower articular apophyses of the upper vertebra being attached to each upper articular apo-physes of the lower vertebra with a bone screw.

Posterior spinal arthrodesis at a facet joint has advantages relative to the other techniques frequently used. The facets of an upper vertebra are fused to the facets of a lower vertebra, such as each lower articular apophyses of the upper vertebra fusing with each upper articular apophyses of the lower vertebra. Bone growth fuses the facet joint for a connection more stable than the bone screws through the facets of the prior art. This technique is in particular less traumatic and has fewer risks. This technique, however, requires using different means from those of other operating techniques, thus the characteristics of the prior art interver-tebral cages, such as those of the aforementioned docu-ments, are not suitable for use for this operating mode.

The intervertebral cages of USPub20200138589, USPub20110230965, USPub20080288076 rely on pressure to maintain orientation of the cage. The same compression and pressure previously exerted on the disc before removal allows the gripping surfaces of these prior art implant devices to be smaller and equally proportional to the height of the cages. The installation is much easier with nearly rotational symmetry of the prior art intervertebral cages.

Implant devices are already known that are suitable for being inserted in a facet joint. WO 2012154653 discloses a wedge element with two opposite faces in contact with corresponding facets. The surface of each face is provided with reliefs to ensure the anchoring, and there are multiple holes suitable for the development of the bone material after a bone graft is deposited. The installation is done by fastening two screws, each screw fastens to a respective apophysis. The prior art implant device for a facet joint remains complex, especially with regard to implementation requiring multiple angles of insertion for the wedge element and each screw. The risk of damage and improper installa-tion of this prior art implant device is very high. Misalign-ment of the bone screws anchors the device with less stability and reliability. The effectiveness of the fusion at the facet joints is inconsistent and unreliable.

BRIEF SUMMARY OF THE INVENTION

Embodiments of the present invention include an implant device for a facet joint that avoid complications of conven-tional spinal fusion at the body of the vertebra, while addresses the required strength and reliability of fusion on the apophyses of the vertebra. The implant device for a facet joint includes a wedge portion and an anchor portion. The anchor portion is made integral with the wedge portion so as to form a central opening. The fusion of the vertebrae occurs through the central opening.

The anchor portion can be comprised of a first face, a second face opposite the first face, and a lateral rim between the first face and the second face. The first face has a length and width greater than a thickness of the lateral rim. The second face also has a length and width greater than the thickness of the lateral rim so as to form a rectangular prism portion. The first face is on a first longest and widest side of the rectangular prism portion. The second face is on a second longest and widest side of the rectangular prism portion. There are a plurality of first notches on the first face and a plurality of second notches on the second face. The anchor portion can be further comprised of a hole extending from the central opening to the lateral rim. The hole can be used for installation of the implant device.

Embodiments of the present invention also include the method of fusing vertebrae. The method includes the step of forming a rectangular cavity between the lower articular apophyses of the upper vertebra and the upper articular apophyses of the lower vertebra. The rectangular cavity has a first longest and widest side on the upper vertebra and a second longest and widest side on the lower vertebra. The implant device is inserted within the rectangular cavity with the first face facing the first longest and widest side and the second face facing the second longest and widest side. The upper vertebra fuses to the first face, and the lower vertebra fuses to the second face. The upper vertebra and the lower vertebra fuse to each other through the central opening.

Further embodiments of the method include an additional implant device and an additional rectangular cavity between an additional lower articular apophyses of the upper vertebra and an additional upper articular apophyses of the lower vertebra. The additional implant device is inserted within the additional rectangular cavity with the analogous alignment of the component and vertebrae parts. The implant device and the additional implant device can be aligned across the upper vertebra so as to fuse both sides of the upper vertebra to the lower vertebra. That is, the implant device and the additional implant device can be generally parallel. Alternatively, the first face of the implant device is cooperative with the additional first face of the additional implant device across the upper vertebra so as to fuse from both sides of the vertebrae. The implant device and the additional implant device are oriented symmetrically across a midline of the upper vertebra. There is no balanced fusion on opposite side of the vertebrae for a strong and reliable fusion on facet joints.

The advantages and features of the implant device according to the invention will emerge more clearly from the following description relative to the appended drawing, which shows one non-limiting embodiment thereof.

BRIEF DESCRIPTION OF THE SEVERAL VIEWS OF THE DRAWINGS

FIG. 5 shows a schematic view of a facet joint, showing an upper vertebra and a lower vertebra.

FIG. 6 shows a schematic view of an embodiment of a rectangular cavity formed between an upper vertebra and a lower vertebra, according to the present invention.

FIG. 7 shows a schematic view of an embodiment of an implant device being inserted into the rectangular cavity of FIG. 6 formed between an upper vertebra and a lower vertebra, according to the present invention.

FIG. 8 shows a schematic view of another embodiment of an implant device and an additional implant device to fuse the upper vertebra and lower vertebra, according to the present invention.

DETAILED DESCRIPTION OF THE INVENTION

Figures 1, 2, 3, 4:
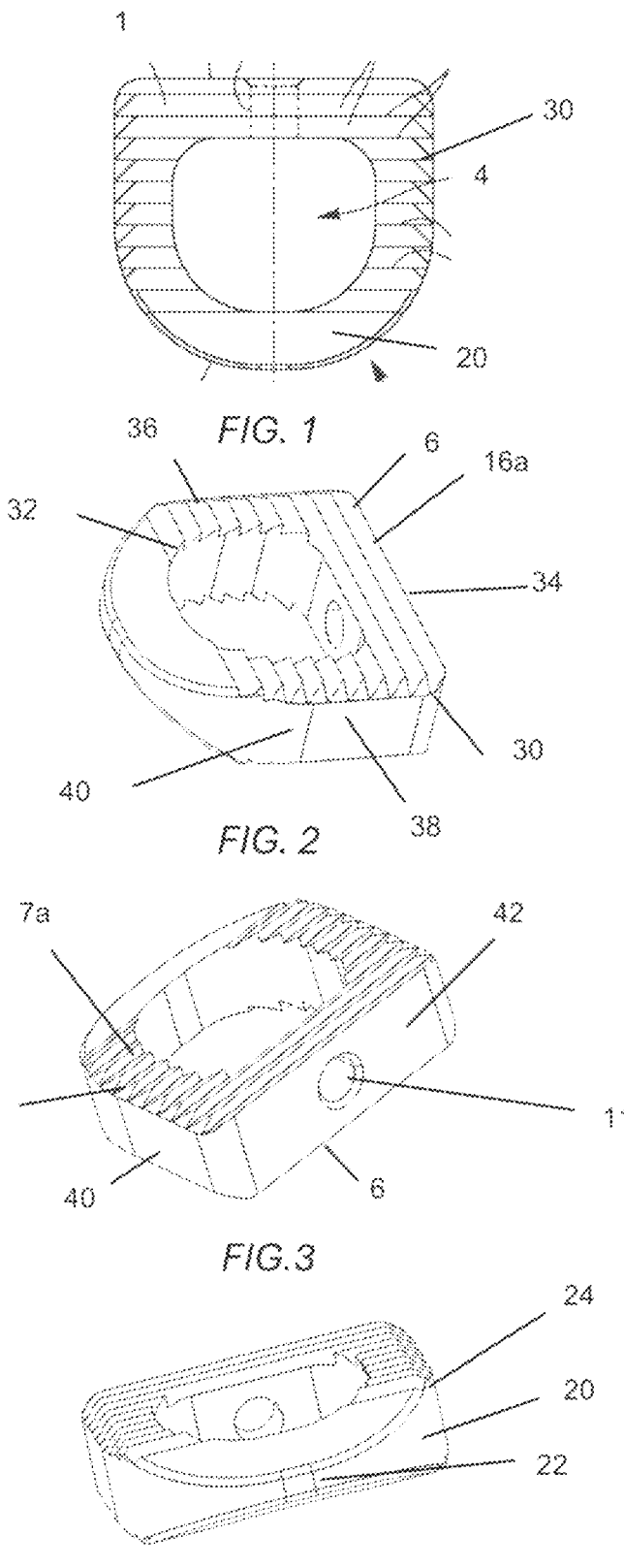
FIG. 1 shows a top plan view of the implant device according to the present invention.
FIG. 2 shows an upper side perspective view of the implant device of FIG. 1.
FIG. 3 shows a rear perspective view of the implant device of FIG. 1.
FIG. 4 shows a front perspective view of the implant device of FIG. 1.

The implant devices for a facet joint must be strong and reliable. Conventional spinal fusion surgery relies on the body of the vertebra, instead of the apophyses or facets. Some posterior spinal fusion surgery even removes an apophysis in order to better access the disc and body of the vertebra. The fusion of a facet joint is stabilizing connection, not the entire fusion of the spine. In the spinal fusion surgeries that do rely on the fusion of the facet joints, there is a great concern for strong attachment between a more fragile part of the vertebra. Without being able to rely as consistently on the pressure and position of a disc, the implant device for a facet joint must be simply and direct to avoid complicated removal on the apophyses.

FIGS. 1-4 show an implant device 1 for a facet joint comprising a wedge portion 20 and an anchor portion 30. The wedge portion 20 has a distal wedge end 22 and a proximal wedge end 24 opposite the distal wedge end. The wedge portion also has increasing thickness from the distal wedge end to the proximal wedge end. The wedge portion is slanted. The anchor portion 30 is made integral with the wedge portion at the proximal wedge end so as to form a central opening 4. The central opening 4 can have a D-shape. The anchor portion has a distal anchor end 32, a proximal anchor end 34 opposite the distal anchor end, a first side anchor end 36 between the distal anchor end and the proximal anchor end, and a second anchor end 38 between the distal anchor end and the proximal anchor end and opposite the first anchor end.

FIGS. 1-4 show that the anchor portion 30 is comprised of a first face 5, a second face 6 opposite the first face, and a lateral rim 40 between the first face and the second face. The first face has a length and width greater than a thickness of the lateral rim. The second face also has a length and width greater than the thickness of the lateral rim so as to form a rectangular prism portion 42. FIGS. 1-4 show that the first face 5 is on a first longest and widest side 15 of the rectangular prism portion and that the second face is on a second longest and widest side 16 of the rectangular prism portion opposite the first longest and widest side 15.

Embodiments of the present invention include a plurality of first notches 7a on the first face; and a plurality of second notches 16a on the second face. Furthermore, the wedge portion can have a curved outer edge 2 at the distal wedge end. The anchor portion can be further comprised of a hole 11 on the proximal anchor end. The hole extends from the central opening to the lateral rim. The hole can be used for installation of the implant device.

The present invention also includes the method of fusing vertebrae, as shown in FIGS. 5-10. The facet joint involves a lower articular apophyses 102 of an upper vertebra 104 and an upper articular apophyses 106 of a lower vertebra 108, as shown in FIG. 5. The method includes the step of forming a rectangular cavity 100 between the lower articular apophyses 102 of the upper vertebra 104 and the upper articular apophyses 106 of the lower vertebra 108, as shown in FIG.

6. The rectangular cavity 100 has a first longest and widest side 110 on the upper vertebra and a second longest and widest side 112 on the lower vertebra.

Figure 9:
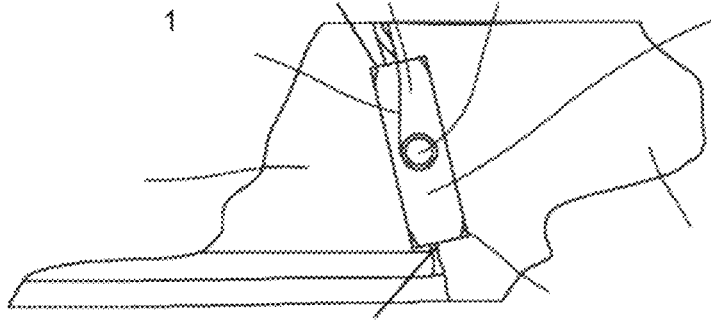
FIG. 9 is a schematic view of the implant device inserted in the rectangular cavity, according to FIG. 7 and FIG. 8.
Figure 10:
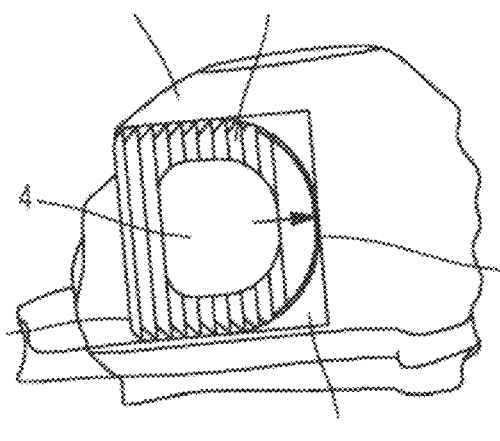
FIG. 10 is a sectional schematic view of the implant device in the rectangular cavity on the lower vertebra.

The method further includes the step of inserting an implant device 1 within the rectangular cavity, as in FIG. 7. The first face 5 faces the first longest and widest side 110 on the upper vertebra, and the second face 6 faces second longest and widest side 112 on the upper vertebra. FIGS. 8-10 show the upper vertebra fusing to the first face, the lower vertebra fusing to the second face, and the upper vertebra and the lower vertebra fusing through the central opening. The method of the present invention avoids complicated drilling and cavity formation on the apophyses, while establishing a strong a reliable fusion on these parts of the vertebrae.

FIG. 8 shows an alternative embodiment of the present invention for a method with an additional implant device 1, and an additional rectangular cavity 200 between an additional lower articular apophyses 202 of the upper vertebra 104 and an additional upper articular apophyses 206 of the lower vertebra 108. The additional rectangular cavity has a corresponding an additional first longest and widest side 210 on the upper vertebra and a corresponding additional second longest and widest side 212 on the lower vertebra. The additional implant device 1 is inserted within the additional rectangular cavity with the analogous alignment of the component and vertebrae parts.

That is, the additional implant device comprises an additional a wedge portion 20 and an additional anchor portion 30 being made integral with the additional wedge portion so as to form an additional central opening 4. The additional anchor portion 30 is comprised of an additional first face 5, an additional second face 6 opposite the additional first face, and an additional lateral rim 40 between the additional first face and the additional second face so as to form an additional rectangular prism portion 42 with the first face on a first longest and widest side 15 of the rectangular prism portion and the second face on a second longest and widest side 16 of the rectangular prism portion opposite the first longest and widest side 15. In the embodiment of the method, the additional first face 5 faces the additional first longest and widest side 210 on the upper vertebra, and the additional second face 6 faces the additional second longest and widest side 212 on the lower vertebra. FIG. 8 shows that implant device and the additional implant device are aligned across the upper vertebra so as to fuse both sides of the upper vertebra to the lower vertebra. The upper vertebra fuses to the additional first face, and the lower vertebra fuses to the additional second face. The upper vertebra and the lower vertebra fuse to each other through the additional central opening.

Embodiments of the method of fusing vertebrae include the alignment of the implant device and the additional implant device as the first face of the implant device being parallel to the additional first face of the additional implant device. Alternatively, the first face of the implant device is cooperative with the additional first face of the additional implant device across the upper vertebra so as to fuse from both sides of the vertebrae. The implant device and the additional implant device are oriented symmetrically across a midline of the upper vertebra so that there is fusion on both sides of the upper vertebra. There is no balanced fusion on opposite side of the vertebrae for a strong and reliable fusion on facet joints.

The present invention avoids the higher risk disc replacement spinal fusion. Both anterior and posterior versions of this intervertebral cage surgery can be avoided. For posterior spinal fusion of the facet joints, the present invention discloses an innovative implant device with a first face on a first longest and widest side of a rectangular prism portion and a second face on a second longest and widest side of the rectangular prism portion and the orientation of the notches on these faces in a rectangular cavity between the vertebrae. Bone plates, bone screws, and intervertebral cages are not compatible with a facet joint or not reliable enough for a strong fusion at the facet joint. The present invention is an implant device and method of fusing vertebrae to address these concerns.

The foregoing disclosure and description of the invention is illustrative and explanatory thereof. Various changes in the details of the illustrated structures, construction and method can be made without departing from the true spirit of the invention.

We claim:

1. An implant device for a facet joint, comprising:

a wedge portion having a distal wedge end and a proximal wedge end opposite said distal wedge end, said wedge portion having increasing thickness from said distal wedge end to said proximal wedge end;

an anchor portion being made integral with said wedge portion at said proximal wedge end so as to form a central opening and having a distal anchor end, a proximal anchor end opposite said distal anchor end, a first side anchor end between said distal anchor end and said proximal anchor end, and a second anchor end between said distal anchor end and said proximal anchor end and opposite said first anchor end, said central opening having a D-shape with a curve of the D-shape corresponding to said proximal wedge end, wherein said anchor portion and said wedge portion are comprised of a first face extending from said anchor portion to said distal wedge end, a second face opposite said first face extending from said anchor portion to said distal wedge end, and a lateral rim between said first face and said second face, said first face having a length and width greater than a thickness of said lateral rim and said second face having a length and width greater than said thickness of said lateral rim so as to form a rectangular prism portion with said first face on a first longest and widest side of said rectangular prism portion and said second face on a second longest and widest side of said rectangular prism portion opposite said first longest and widest side;

a plurality of first notches on said first face from said anchor portion to said wedge portion and from said proximal wedge end toward said distal wedge end; and a plurality of second notches on said second face from said anchor portion to said wedge portion and from said proximal wedge end toward said distal wedge end.

2. The implant device, according to claim 1, wherein said wedge portion is further comprised of a curved outer edge at said distal wedge end.

3. The implant device, according to claim 1, wherein said anchor portion is further comprised of a hole on said proximal anchor end, said hole extending from said central opening to said lateral rim.

4. A method of fusing vertebrae, comprising the steps of:

forming a rectangular cavity between a lower articular apophyses of an upper vertebra and an upper articular apophyses of a lower vertebra, said rectangular cavity having a first longest and widest side on said upper vertebra and a second longest and widest side on said lower vertebra;

inserting an implant device, according to claim 1, within said rectangular cavity, said wedge portion entering said rectangular cavity before said anchor portion, said first face corresponding to said anchor portion facing said first longest and widest side on said upper vertebra, said second face corresponding to said anchor portion facing said second longest and widest side on said upper vertebra;

fusing said upper vertebra to said plurality of first notches on said first face corresponding to said anchor portion;

fusing said lower vertebra to said plurality of second notches on said second face corresponding to said anchor portion;

fusing said upper vertebra and said lower vertebra through said central opening;

fusing said upper vertebra to said plurality of first notches on said first face corresponding to said wedge portion; and fusing said lower vertebra to said plurality of second notches on said second face corresponding to said wedge portion.

5. The method of fusing vertebrae, according to claim 4, further comprising the steps of:

forming an additional rectangular cavity between an additional lower articular apophyses of said upper vertebra and an additional upper articular apophyses of said lower vertebra, said additional rectangular cavity having an additional first longest and widest side on said upper vertebra and an additional second longest and widest side on said lower vertebra;

inserting an additional implant device within said an additional rectangular cavity, wherein said additional implant device comprises;

an additional wedge portion having an additional distal wedge end and an additional proximal wedge end opposite said additional distal wedge end, said additional wedge portion having increasing thickness from said additional distal wedge end to said additional proximal wedge end; and an additional anchor portion being made integral with said additional wedge portion so as to form an additional central opening, said additional central opening having a respective D-shape with a respective curve of the respective D-shape corresponding to said additional proximal wedge end, wherein said additional anchor portion and said additional wedge portion are comprised of an additional first face extending from said additional anchor portion to said additional distal wedge end, an additional second face extending from said additional anchor portion to said additional distal wedge end and being opposite said additional first face, and an additional lateral rim between said additional first face and said additional second face so as to form an additional rectangular prism portion with said additional first face on a first longest and widest side of said additional rectangular prism portion and said additional second face on a second longest and widest side of said additional rectangular prism portion opposite said first longest and widest side;

wherein said additional first face faces said additional first longest and widest side on said upper vertebra, wherein said additional second face faces said additional second longest and widest side on said lower vertebra, and wherein said implant device and said additional implant device are aligned across said upper vertebra so as to fuse both sides of said upper vertebra to said lower vertebra;

fusing said upper vertebra to said additional first face corresponding to said additional anchor portion;

fusing said lower vertebra to said additional second face corresponding to said additional anchor portion;

fusing said upper vertebra and said lower vertebra through said additional central opening;

fusing said upper vertebra to said additional first face corresponding to said additional wedge portion; and fusing said lower vertebra to said additional second face corresponding to said additional wedge portion.

6. The method of fusing vertebrae, according to claim 5, wherein said first face of said implant device is cooperative with said additional first face of said additional implant device across said upper vertebra.

7. The method of fusing vertebrae, according to claim 5, wherein said implant device and said additional implant device are oriented symmetrically across a midline of said upper vertebra.

* * * * *